United States Patent [19]

Hamilton et al.

[11] Patent Number: 4,738,954
[45] Date of Patent: Apr. 19, 1988

[54] NOVEL $N^6$-SUBSTITUTED-5'-OXIDIZED ADENOSINE ANALOGS

[75] Inventors: Harriet W. Hamilton, Chelsea, Mich.; William C. Patt, Feasterville, Pa.

[73] Assignee: Warner-Lambert Company, Morris Plains, N.J.

[21] Appl. No.: 795,557

[22] Filed: Nov. 6, 1985

[51] Int. Cl.$^4$ .................. A61K 31/70; C07H 17/00; C07H 19/06

[52] U.S. Cl. .......................... 514/46; 536/26

[58] Field of Search ............................ 514/46; 536/26

[56] References Cited

U.S. PATENT DOCUMENTS

| 3,838,147 | 9/1974 | Pohlke et al. ............... 260/112.5 R |
| 3,914,415 | 10/1975 | Stein et al. ....................... 514/46 |
| 3,966,917 | 6/1976 | Prasad et al. ..................... 514/46 |
| 3,992,531 | 11/1976 | Prasad et al. ..................... 514/46 |
| 4,104,462 | 8/1978 | Fischer et al. ..................... 536/26 |
| 4,224,438 | 9/1980 | Fauland et al. ................... 536/26 |
| 4,479,942 | 10/1984 | Yamashita et al. ................ 514/46 |

FOREIGN PATENT DOCUMENTS

| 0066918 | 12/1982 | European Pat. Off. . |
| 2632951 | 2/1977 | Fed. Rep. of Germany . |
| 2632950 | 2/1977 | Fed. Rep. of Germany . |
| 2610986 | 1/1978 | Fed. Rep. of Germany . |
| WO86/00310 | 1/1986 | PCT Int'l Appl. . |

Primary Examiner—Nicky Chan
Attorney, Agent, or Firm—Joan Thierstein

[57] ABSTRACT

Novel $N^6$-substituted-5'-oxidized adenosine analogs, and pharmaceutical compositions, methods of use or processes to make therefore. The novel adenosines have utility for the treatment of hypertension, coronary insufficiency, psychosis, pain, angina, and heart failure.

15 Claims, No Drawings

NOVEL N⁶-SUBSTITUTED-5'-OXIDIZED ADENOSINE ANALOGS

BACKGROUND OF THE INVENTION

6-Substituted adenosines are known. Additionally, variations at the 5' position on a ribose substituent of adenosines are known.

For example, DT 2632951 described in Derwent Abstract No. 11515Y/07 and DT No. 2610-986 which is equivalent to U.S. Pat. No. 4,122,172 described in Derwent Abstract No. 76155X/41 disclose a compound of the formula XX wherein Z is defined as various substituents attached at the 5' ribose position of an adenosine through a carbonyl. DT No. 2730-846 and DT No. 2632-950 are more specific disclosures to variations of adenosines generally of formula XX. Numerous other references disclose various 5' substituents having essentially the formula XX.

6-Substituted adenosines having various 5' substituents include the compounds of formula XXI (U.S. Pat. No. 3,830,795-Derwent Abstract No. 62864V35), XXII (U.S. Pat. No. 3,931,401-Derwent Abstract No. 05487X/03), XXIII where $R^{IV}$ and $R^{V}$ may be hydrogen, acyl or together a diacyl residue of an aliphatic or aromatic dicarboxylic acid (DT 2606532-Derwent Abstract No. 6731X/36), XXIV where $R^{VI}$, may be hydrogen or allyl (U.S. Pat. Nos. 3,914,414 and 3,914,415-Derwent Abstract No. 74014W/44 and 74015W/44 respectively). Similarly, EP Application No. 0066918 discloses 6-substituted amino compounds wherein the 6-substitutions are 1–4C alkyl or phenyl of formula XXV having Z' defined as $CONR^{IV}R^{V}$ or $CO_2R^{V}$.

Specifically, U.S. application Ser. No. 772,315 filed Sept. 6, 1985 now pending which is a continuation in part of U.S. application Ser. No. 665,217 filed Oct. 26, 1984, now abandoned, U.S. application Ser. No. 771,589 filed Sept. 5, 1985, now U.S. Pat. No. 4,616,003 issued Oct. 7, 1986 which is a continuation of application Ser. No. 665,229 filed Oct. 26, 1984, now abandoned, and U.S. application Ser. No. 771,590 filed Sept. 5, 1985, now pending, which is a continuation in part of application Ser. No. 665,218 filed Oct. 26, 1984, now abandoned disclose 5' deoxy, 5' deoxy-5'-methylthio, or 5'-deoxy-5'-halogen variations of 6-Substituted adenosines. Further, U.S. application Ser. No. 625,450 filed June 28, 1984 discloses N⁶ substituted and 5'-N-substituted Carboxamidoadenosine derivatives as cardiac vasodilators. All of these U.S. applications except U.S. application Ser. No. 625,450 are hereby incorporated by reference.

U.S. Pat. No. 3852268 described in Derwent Abstract No. 88536V/51 and U.S. Pat. No. 3853846 described in Derwent Abstract No. 90059V/52 disclose inosines having various 5' substituents.

Further, references such as U.S. Pat. No. 3,922,261, German Application No. 2,402,804 and U.S. Pat. No. 4,501,735 disclose various 6-benzocycloalkyl adenosines. U.S. Pat. No. 3,502,649 discloses 6-arylisopropyladenosine and U.S. Ser. No. 756,922 filed July 18, 1985 issued Apr. 14, 1987 as U.S. Pat. No. 4,657,898 which is a continuation in part of U.S. Ser. No. 519,284 discloses 6-diarylalkyladenosine. Also disclosed in U.S. Pat. No. 3,590,029 are N-6-cycloalkyladenosines. However, none of these references teach a 5' variation on the ribose moiety of the disclosed adenosines.

Therefore, none of the above noted references disclose the adenosines of the present invention. Particularly, there is no teaching to the combination of substituents at the 6 and 5' positions of the present novel adenosines. Further, no teaching in the above noted references shows preparation for the present invention adenosines having the N6 substituted-5'-substituted moieties defined hereinafter.

SUMMARY OF THE INVENTION

Accordingly the present invention relates to a compound of the formula (I)

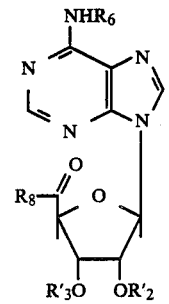

wherein $R_6$ is (a)

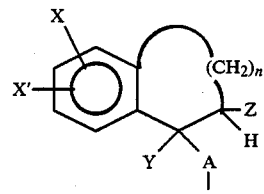

wherein X and X' are each independently absent, lower alkyl, lower alkoxy, hydroxy, lower alkanoyl, nitro, trifluoromethyl, halogen, amino, monoloweralkyl- or diloweralkyl-amino, or X and $X^1$ taken together are a methylenedioxy group; n is 1 to 4, Z is hydrogen, lower alkyl, or OR wherein R is hydrogen, lower alkyl or lower alkanoyl; A is a bond or a straight or branched chain alkylene of from one to four carbon atoms.

(b) cycloalkyl of from 3 to 7 ring carbons or cycloalkyl of from 3 to 7 ring carbons substituted by lower alkyl;

(c)

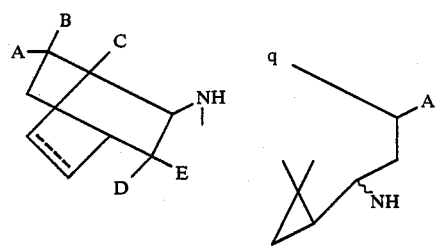

in which NH— is either endo or exo; ==== is a double or single bond; n is zero, one or two; A and B are either both hydrogen or both methyl; D and E are also either both hydrogen or both methyl; C is hydrogen or methyl; and the proviso that when D and E are methyl then A and B are both hydrogen and C is methyl but when D and E are hydrogen then A, B, and C are all hydrogen or all methyl; q is —C(CH$_3$)$_2$—, —CH$_2$—, —CH$_2$CH$_2$—, or —CH=CH;

(d)

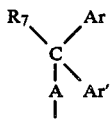

wherein R$_7$ is hydrogen, hydroxy, lower alkyl, lower carboalkoxy, or lower alkanoyloxy; A is as defined above; and Ar and Ar' are each independently (i) phenyl (ii) phenyl substituted by trifluoromethyl, halogen, hydroxy, thiol, lower alkoxy, lower thioalkoxy, lower alkanoyloxy, lower alkyl, nitro, amino, lower S(O)$_b$-alkyl wherein b is 0, 1, or 2, or sulfonamide, or (iii) 2, 3, or 4-pyridyl, 2- or 3-thienyl, 2- or 3-furanyl, or (iv) naphthyl; or (e)

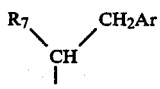

wherein R$_7$ and Ar are as defined above; R'$_3$ and R'$_2$ are each independently hydrogen, acyl of from 1 to 6 carbons, alkanoyl of from 1 to 6 carbons, benzoyl, benzoyl substituted by lower alkyl, lower alkoxy, trifluoromethyl or halogen, or R'$_2$ and R'$_3$ taken together are a five membered ring having a total of up to twenty carbons, such as isopropylidene; and R$_8$ is (a) OR'$_5$ wherein R'$_5$ is hydrogen, lower alkyl of from one to six carbons, or cycloalkyl of from three to seven ring carbons optionally substituted by lower alkyl of from one to four carbons, or (b) NR$_3$R$_4$ wherein R$_3$ and R$_4$ are independently hydrogen, lower alkyl of from one to six carbons, or cycloalkyl of from three to seven ring carbons optionally substituted by lower alkyl; its diastereomers, or a pharmaceutically acceptable acid addition salt thereof.

The present invention also relates to a pharmaceutical composition comprising a therapeutically effective amount of a compound of the above formula I and a pharmaceutically acceptable carrier. Additionally, the present invention is a method of treating mammals, including humans suffering from hypertension, coronary insufficiency, psychosis, pain, angina or heart failure and has a favorable antiaggregation of platelets function, by administering to such mammals an effective amount of a compound of the Formula I as defined above in a unit dosage form.

Finally, the present invention includes a process for the preparation of the compound of formula I above.

DETAILED DESCRIPTION OF THE EMBODIMENTS

In the compounds of the formula I, the term "lower alkyl" is meant to include a straight or branched alkyl group having from 1 to 6 carbon atoms, inclusive, such as methyl, ethyl, propyl, isopropyl, butyl, sec-butyl, isobutyl, tert-butyl, and the like.

Halogen, particularly, includes fluorine, chlorine, or bromine.

Lower alkoxy is O-alkyl of from 1 to 6 carbon atoms as defined above for "lower alkyl".

Lower alkanoyl or alkanoyloxy is a straight or branched alkyl-C, or straight or branched alkyl-C-O group, respectively, of from 1 to 6 carbon atoms in the alkyl chain as defined above.

Lower thioalkoxy is alkyl-S group of from one to six carbon atoms in the alkyl chain as defined above.

The compounds of formula I are useful both in the free base form and in the form of acid addition salts. Both forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfate, ethanesulfonate, benzenesulfonate, p-toluenesulfonate, and the like, respectively.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The compounds of the invention may contain an asymmetric carbon atom. The invention includes the individual diastereomers and mixtures thereof. The individual diastereomers may be prepared or isolated by methods known in the art.

The preferred embodiments include (R)-N-6-[(2-phenyl-1-methyl-)ethyl]adenosine-5'-ethylcarboxamide, (R)-N-6-(1-indanyl)adenosine-5'-ethylcarboxamide, N-6-(2,2-diphenylethyl)adenosine-5'-ethylcarboxamide, N-6-cyclopentyladenosine-5'-ethylcarboxamide and N-6-(2,2-diphenylethyl-5-adenosine-5'-ethylcarboxylate.

Most preferred is (R)-N-6-[(2-phenyl-1-methyl)ethyl]adenosine-5'-ethylcarboxamide.

The compounds of formula I may generally be synthesized from an inosine of the formula V wherein R'$_2$ and R'$_3$ are taken together to form the alkylidene defined above by the method shown in Scheme I. The inosine of formula V is treated with thionyl chloride at from 0° C. to 60° C., preferably about 40° C., for from 2 to 8 hours or about 4 hours. A mixture of an alcohol of formula HOR'$_5$ wherein R'$_5$ is as defined above and the treated inosine is stirred at a temperature of from about −20° C. to 20° C. or preferably about 0° C. The alkylidene moiety is removed by treatment with an agent from among those known in the art, such as formic acid. The resulting compound of formula IV wherein R'$_5$ is as defined above is then treated to obtain a compound of formula III having protecting groups such that R'$_2$ and R'$_3$ are preferably alkanoyl, benzoyl, or benzoyl substituted by lower alkyl, lower alkoxy, or halogen but may be other protecting groups as well. This protected product is then treated with tetraethyl ammonium chloride, dimethyl aniline and phosphoroyl chloride in dimethylformamide (DMF) at a temperature of from 80° C. to 120° C., preferably about 100° to 115° C. to yield the compound of formula II wherein R'$_5$, R'$_2$ and R'$_3$ are as defined for the compound of formula III.

Finally, the compound of formula II is reacted with a compound of formula NH$_2$R$_6$ in a solvent such a methanol, ethanol or the like in the presence of a base such a triethylamine. The resulting compound of formula $I_3$ may optionally be either deprotected or further, reacted by treatment with a compound of formula $NHR_3R_4$ wherein $R_3$ and $R_4$ are as defined above to give a compound of formula of $I_1$ or $I_2$ respectively.

The products of the reactions described herein are isolated by conventional means such as extraction, distillation, chromatography, and the like.

The requisite starting materials or materials from which the starting materials can be prepared in the above described processes can be prepared, are available commercially, or are prepared using methods known in the literature.

The compounds of formula I of the present invention have favorable ratio of affinities for adenosine receptors designated A1 and A2 receptors and highly desirable central nervous system and cardiovascular activities, such as analgesic, antipsychotic, or antihypertensive. In addition, these adenosine compounds also have antiaggretory activity with platelets. Particularly, the compounds of formula I are active in animal tests which are predictive of neuroleptic activity for the treatment of major pschosis such as schizophrenia.

The compounds of formula I also show antihypertensive activity in animal tests and therefore, are useful for the treatment of high blood pressure. They also improve coronary circulation and have a favorable effect on platelet aggregation, and are therefore useful in the treatment of heart disease.

Additionally, the compounds of the present invention also have analgesic properties and as such, are useful in the treatment of pain.

PHARMACOLOGICAL EVALUATION

Adenosine Receptor Binding—A$_1$ Receptor Affinity (RBA1)

Preparation of Membranes

Whole brain minus cerebellum and brainstem from male Long Evans rats (105–200 g) was homogenized in 30 volumes of ice-cold 0.05M Tris-HCl buffer pH 7.7 using a Brinkman Polytron PT-10, (setting number 6 for 20 seconds) and centrifuged for ten minutes at 20,000×g (Sorvall RC-2), 4° C. The supernatant was discarded, and the pellet was resuspended and centrifuged as before. The pellet was resuspended in 20 ml Tris-HCl buffer containing two International Units/ml of adenosine deaminase (Sigma type III from calf intestinal mucosa), incubated at 37° C. for 30 minutes, then subsequently at 0° C. for ten minutes. The homogenate was again centrifuged, and the final pellet was resuspended in ice-cold 0.05M Tris-HCl buffer pH 7.7 to a concentration of 20 mg/ml original wet tissue weight and used immediately.

Assay Conditions

Tissue homogenate (10 mg/ml) was incubated in 0.05M Tris-HCl buffer pH 7.7 containing 1.0 nM (($^3$H))-N$^6$-cyclohexyladenosine ([$^3$H]-CHA) with or without test agents in triplicate for one hour at 25° C. Incubation volume was 2 ml. Unbound [$^3$H]-CHA was separated by rapid filtration under reduced pressure through Whatman glass fiber (GF/B) filters. The filters were rinsed three times with 5 ml of ice cold 0.05M Tris-HCl buffer pH 7.7. The radio-labeled ligand retained on the filter was measured by liquid scintillation spectrophotometry after shaking the filters for one hour or longer on a mechanical shaker in 10 ml of Beckman Ready-Solv HP scintillation cocktail.

Calculations

Nonspecific binding was defined as the binding which occured in the presence of 1 mM theophylline. The concentration of test agent which inhibited 50% of the specific binding (IC$_{50}$) was determined by nonlinear computer curve fit. The Scatchard plot was calculated by linear regression of the line obtained by plotting the amount of radioligand bound (pmoles/gram of tissue) versus $$\left(\left(\frac{\text{bound radioligand}}{\text{free radioligand}}\right)\right).$$

Since the amount of radioligand bound was a small fraction of the total amount added, free radioligand was defined as the concentration of (nM) of radioligand added to the incubation mixture. The Hill coefficient was calculated by linear regression of the line obtained by plotting the log of the bound radioligand vs the log of the $$\left(\left(\frac{\text{bound radioligand}}{B_{max} - \text{bound radioligand}}\right)\right).$$

The maximal number of binding sites (B$_{max}$) was calculated from the Scatchard plot.

Adenosine Receptor Binding—A$_2$ Receptor Affinity (RBA2)

Tissue Preparation

Brains from 200–500 g mixed sex Sprague-Dawley rats were purchased from Pel-Freez (Rogers, Arkansas). Fresh brains from male Long-Evans hooded rats (Blue Spruce Farms, Altamont, NY) gave essentially identical results. Brains were thawed and then kept on ice while the striata were dissected out. Striata were disrupted in 10 vol of ice-cold 50 mM Tris.HCl (pH 7.7 at 25° C., pH 8.26 at 5° C.) (Tris) for 30 seconds in a Polytron PT-10 (Brinkmann) at setting 5. The suspension was centrifuged at 50,000×g for ten minutes, the supernatant discarded, the pellet resuspended in 10 vol ice-cold Tris as above, recentrifuged, resuspended at 1 g/5 ml, and stored in plastic vials at −70° C. (stable for at least six months). When needed, tissue was thawed at room temperature, disrupted in a Polytron, and kept on ice until used.

Incubation Conditions

All incubations were for 60 minutes at 25° C. in 12×75 mm glass tubes containing 1 ml Tris with 5 mg original tissue weight of rat weight of rat striatal membranes, 4 nM [$^3$H]-N-ethyl adenosine-5'-carboxamide ([$^3$H]NECA), 50 nM N$^6$-cyclopentyladenosine (to eliminate A$_1$ receptor binding), 10 mM MgCl$_2$, 0.1 units/ml of adenosine deaminase and 1% dimethylsulfoxide. N$^6$-Cyclopentyladenosine was dissolved at 10 mM in 0.02N HCl and diluted in Tris. Stock solutions and dilutions of N$^6$-cyclopentyladenosine could be stored at −20° C. for several months. Test compounds were dissolved at 10 mM in dimethylsulfoxide on the same day as the experiment, and diluted in dimethylsulfoxide to 100× the final incubation concentration. Control incubations received an equal volume (10 μl) of dimethylsulfoxide; the resulting concentration of dimethylsulfoxide had no effect on binding. [$^3$H]NECA was diluted to 40 nM in Tris. The membrane suspension (5 mg/0.79 ml) contained sufficient MgCl$_2$ and adenosine deaminase to give 10 mM and 0.1 units/ml, respectively, final concentration in the incubation. For test compounds with IC$_{50}$ values less than 1 μM, the order of additions was test compound (10 μl), N$^6$-cyclopentyladenosine (100 μl), [$^3$H]NECA (100 μl), and membranes (0.79 ml). For test compounds with IC$_{50}$ values greater than 1 μM and limited water solubility, the order of additions (same volumes) was test compound, membranes, N$^6$-cyclopentyladenosine, and [$^3$H]NECA. After all additions, the rack of tubes was vortexed, and the tubes were then incubated for 60 min at 25° C. in a shaking water bath. The rack of tubes was vortexed an additional time halfway through the incubation.

Incubations were terminated by filtration through 2.4 cm GF/B filters under reduced pressure. Each tube was filtered as follows: the contents of the tube were poured on the filter, 4 ml of ice-cold Tris were added to the tube and the contents poured onto the filter, and the filter was washed twice with 4 ml of ice-cold Tris. The filtration was complete in about twelve seconds. Filters were put in scintillation vials, 8 ml of Formula 947 scintillation fluid added, and the vials left overnight, shaken, and counted in a liquid scintillation counter at 40% efficiency.

Data Analysis

Nonspecific binding was defined as binding in the presence of 100 μM N$^6$-cyclopentyladenosine, and specific binding was defined as total binding minus nonspecific binding. The IC$_{50}$ was calculated by weighted nonlinear least squares curve-fitting to the mass-action equation.

$$Y = T - S \cdot \frac{D}{D+K}$$

where
Y is cpm bound
T is cpm total binding without drug
S is cpm specific binding without drug
D is the concentration of drug and
K is the IC$_{50}$ of the drug Weighting factors were calculated under the assumption that the standard deviation was proportional to the predicted value of Y. Nonspecific binding was treated as a very large (infinite) concentration of drug in the computer analysis.

The IC$_{50}$ values (nM) for adenosine A$_1$ and A$_2$ receptor affinity are reported in the table.

| Example Number | RBA-1 (nM) | RBA-2 (nM) |
|---|---|---|
| 1 | 2 | 70 |
| 2 | 29 | 161 |
| 3 | 16 | 25 |
| 4 | 0.9 | 198 |
| 5 | 291 | 468 |
| 6 | 49 | 8 |
| 7 | 16 | 2680 |
| 8 | 4 | 12400 |

ANTIPSYCHOTIC EVALUATION

The compounds of the invention are new chemical substances which are useful as pharmaceutical agents for the treatment of psychoses. The antipsychotic activity of representative compounds of the invention was established by the Mouse Activity and Screen Test Procedure (MAST) described below.

Animals

Nine unfasted Swiss-Webster male mice weighing 20–30 g are equally divided into three groups for each drug dose to be tested. That is, data for each dose level was generated by three separate groups of three mice each.

Drugs

A minimum of three dose levels (10, 30, and 100 mg/kg) are tested for each drug. Treatments are administered intraperitoneally one hour prior to testing. All dosages are calculated as parent compound and given in volumes of 10 ml/kg. Compounds are dissolved or suspended in 0.2% Methocel. Control animals are injected with Methocel.

Testing:

A two part testing procedure is started one hour postinjection. First, the screen test (ST) is performed (see *Pharmac. Biochem. Behav.* 6, 351–353, 1977). Briefly this test consists of placing mice on individual wire screens which are then rotated 180 degrees at the start of a 60 second observation period. The number of mice falling off the inverted screen is recorded.

Immediately following the screen test, the final phase of testing is initiated by placing each group of three mice in one actophotometer (*Life Sciences*, 22, 1067–1076, 1978). The actophotometer consists of a cylindrical chamber whose center is occupied by another cylinder which contains the illumination for six photocells located on the perimeter of the chamber. Six light-beam interruptions equal one count. Locomotor activity is recorded by computer at ten minute intervals for 60 minutes.

Data:

The data obtained from the screen test are expressed as percent of mice falling off the screen. Data derived from locomotor activity of drug treated mice are compared to the activity of vehicle treated animals and are expressed as percent inhibition of spontaneous locomotion. All percentages reported for inhibition of locomotion (LI) are based upon data accumulated for one hour. Both phases of testing are graded: A=60–100%; C=31–59%; and N=0–30%. An overall dose rating is obtained by the following criteria:

| Inhibition of Locomotion Rating | with | Screen Test Failure Rating | = | Dose Rating |
|---|---|---|---|---|
| A | — | N or C | = | A |
| A | — | A | = | C |
| C | — | N or C | = | C |
| | | All other combinations | = | N |

LAD refers to the lowest dose at which an A rating is achieved. Compounds which exhibit an overall dose rating of A at a dose of 100 milligrams/kilogram or less are considered active. Utilizing this procedure, an overall dose rating of A was obtained for the noted compound at the indicated dose. The compounds are identified in the Examples.

| Example | Dose (mg/kg) | Inhibition of mouse locomotor activity (%) | Screen test failure (%) |
|---|---|---|---|
| 1 | 0.01 | −8 | 0 |
| | 0.03 | 18 | 0 |
| | 0.1 | 91 | 33 |

-continued

| Example | Dose (mg/kg) | Inhibition of mouse locomotor activity (%) | Screen test failure (%) |
| --- | --- | --- | --- |
|   | 0.3 | 75 | 11 |
|   | 1 | 92 | 33 |
|   | 3 | 99 | 88 |
|   | 10 | 99 | 100 |
|   | 30 | 99 | 100 |
| 3 | 0.1 | 20 | 0 |
|   | 0.3 | 1 | 0 |
|   | 1 | 72 | 0 |
|   | 3 | 92 | 0 |
|   | 10 | 90 | 11 |
|   | 30 | 93 | 33 |
| 4* | 0.1 | 33 | 22 |
|   | 0.3 | 36 | 6 |
|   | 1 | 81 | 17 |
|   | 3 | 84 | 22 |
|   | 10 | 84 | 72 |
| 5 | 3 | −4 | 11 |
|   | 10 | 0 | 0 |
|   | 30 | 2 | 0 |
| 6 | 0.03 | 21 | 0 |
|   | 0.1 | 30 | 0 |
|   | 0.3 | 82 | 0 |
|   | 1.0 | 87 | 11 |
|   | 3.0 | 88 | 11 |
|   | 10 | 90 | 0 |
| 9* | 0.1 | 37 | 33 |
|   | 0.3 | 69 | 11 |
|   | 1.0 | 89 | 44 |

*This was done orally in rats, rather than IP in mice.

ANTIHYPERTENSIVE EVALUATION (AHP3)

The usefulness of the compounds of the present invention as antihypertensive agents is demonstrated by their effectiveness in standard pharmacological test procedures, for example, in causing a significant decrease in mean arterial blood pressure in the conscious rat. This test procedure is described in the following paragraphs.

A Method for the Direct Monitoring of Aortic Blood Pressure and Heart Rate from Conscious Rats The continous monitoring of pulsatile blood pressure (BP) from unrestrained conscious rats surgically equipped with polyethylene cannulas was accomplished by means of a computer assisted data capture scheme (CADCS). The basic elements of the methodology are the cannulation procedure and the CADCS.

Method
Cannulation Procedure:

Rats were anesthetized with Telazol (1:1 tiletamine HCl and zolazepam HCl); 20–40 mg/kg IM and the descending aorta exposed via a midline incision. Cannulas fabricated from polyethylene tubing were inserted into the aorta via an undersized puncture hole below the renal arteries. The puncture hole was made by a 23 G disposable needle with a section of the aorta clamped off above and below the puncture site. The cannulas, consisting of a PE100 (0.86 mm ID) body and a PE50 (0.58 mm ID) tip, were attached to a trocar, inserted through the psoas muscle, and passed subcutaneously along the midline of the back and externalized between the ears. The cannulas were anchored to the psoas muscle and between the scalulae (3-0 green braided suture). The midline incision was closed in two steps (muscle first, skin second) using contiuous over-and over sutures (4-0 chronic). Each rat was then given penicillin 30,000 units subcutaneously (Penicilling G Procaine Sterile Suspension).

The rats were fitted with a harness-spring-swivel assembly designed to protect the cannula and to provide the rat relative freedom of movement. The harnesses were fabricated from nylon hook and loop tape cemented to a metal plate to which spring wires (18-8 stainless steel) were attached to brass swivels. Each polyethylene cannula was channeled through a spring and connected through a swivel to a pressure transducer (Model P23Gb; Statham Instruments; Hato Rey, Puerto Rico) and an infusion pump (Sage model 234-7; Orion Research, Cambridge, MA) by means of PE100 tubing. While on test, each rat received a continuous slow infusion of heparinized saline solution (approximately 400 1 or 40 units of heparin per 24 hours period) to prevent clot formation. Additional "flushes" of the cannula with heparinized saline were carried out when the aortic pluse pressure (systolic minus diastolic) was less than 25 mm Hg.

CADCS:

The pulsatile blood pressure and heart rate of each of 32 rats was monitored every minute by means of two in-laboratory microcomputers communicating directly with a data concentrator computer. The data were first stored on the data concentrator disk and then transferred to a magnetic tape for analysis and report generation by the main research computer. The overall scheme involved modulating the primary signal from the pressure transducer, generating the primary data set of the one-minute values for systolic, diastolic, and mean blood pressures and heart rate by the in-lab microcomputer and the storage, analysis, and report generation by the main research computer.

The transducers were connected to analog signal conditioning modules. The modules provided a regulated excitation voltage for the transducers, amplification as required to interface the microprocessors and an active low pass filter to compensate for the pressure wave form distortion produced by the flexible, fluid filled, narrow cannula. The distortion was 22–26 Hz and this provided a reliable estimate of both systolic and diastolic blood pressure.

The microcomputers (one for each of two groups of 16 rats) were connected to the input components through the module interface units, an analog-to-digital converter for the pressure wave form signal and the digital inputs for the dose and event marker switches. The microcomputer controlled the sequential acquisition of data from the modular interface units through an internal synchronous time-of-day clock/time base generator. Utilizing the time base generator as a reference, the blood pressure values and the marker switch status for each of the 32 stations were sampled every ten msec. The microcomputer processed each blood pressure sample as it was received to produce "running average" values for heart rate, and mean, systolic and diastolic blood pressures.

When tested by the tested above procedure, compounds of examples as noted produced the following changes in MAP (mean arterial pressure) and heart rate. LAD refers to the lowest dose tested at which a 10% reduction in blood pressure for four consecutive hours is achieved.

| Antihypertensive Evaluation MAP = Mean Arterial Pressure HR = Heart Rate | | | | | | | |
|---|---|---|---|---|---|---|---|
| Example Number | mg/kg | | Hour | | | | |
| | | | 1 | 3 | 5 | 7 | 9 |
| 1 | 3 | MAP | ↓69% | ↓69% | ↓68% | ↓69% | ↓72% |
|   |   | HR  | ↓66% | ↓65% | ↓61% | ↓62% | ↓69% |
| 3 | 1 | MAP | ↓4%  | ↑11% | 0%   | ↓1%  | ↓5%  |
|   |   | HR  | ↑8%  | ↑18% | 0%   | ↑8%  | ↓2%  |
| 4 | 3 | MAP | ↓60% | ↓57% | ↓51% | ↓60% | ↓63% |
|   |   | HR  | ↓57% | ↓59% | ↓46% | ↓47% | ↓60% |
| 5 | 10| MAP | ↓6%  | ↓10% | 0%   | ↓6%  | ↓11% |
|   |   | HR  | ↑1%  | ↓3%  | ↑4%  | ↓3%  | ↑1%  |
| 6 | 10| MAP | ↓28% | ↓26% | ↓34% | ↓26% | ↓26% |
|   |   | HR  | ↑31% | ↑37% | ↑29% | ↑31% | ↑36% |
| 8 | 10| MAP | ↓5%  | 0%   | ↓5%  | ↓5%  | ↑3%  |
|   |   | HR  | ↓25% | ↓17% | ↓10% | ↑2%  | ↑7%  |

ANTITHROMBOCYTE AGGREGATION TEST-IN VITRO (ATA-8)

Source and Preparation of Platelet Suspensions

Blood is collected from Community Research Clinic volunteers who have not ingested aspirin or other non-steroidol antiinflammatory drugs within the preceeding two weeks and have not eaten within the nine hours before blood draw. Blood is taken in 4.5 ml portions in Vacutainer No. 6462S silicone-coated tubes or equivalent containing 0.5 ml of 3.8% trisodium citrate. Usually six or eight portions of 4.5 ml are drawn from each volunteer. The blood collected from three or four volunteers is pooled prior to centrifugation. The pooled blood is put in 50 ml polyethylene tubes and centrifuged at 80×g (ca 600 rpm) for 20 min in an International Model K centrifuge at room temperature. A portion of the supernatant platelet-rich plasma (PRP) is removed and set aside, and the remaining blood sample is recentrifuged at 1400×g (ca 2800 rpm) for 15 min to prepare platelet-poor plasma (PPP). The platelet count of the PRP is determined with a Coulter Thromobocounter. The PRP is adjusted to a count of 250,000 platelets per microliter using the PPP.

Preparation of Drug Solutions

Text drugs are dissolved in small amounts of DMSO (dimethylsulfoxide) followed by dilution with saline. The final concentration of DMSO in the test samples during aggregation never exceeds 1%, a concentration without effect on aggregability of the platelets. Lower concentrations of the drugs are prepared by serial dilution with saline.

Technique of Aggregation Measurement

Platelet-rich plasma adjusted to 250,000 platelets per microliter is distributed in 0.36 ml aliquots into silicone-coated cuvettes of 0.312 inch diameter. Addition of drug solution or saline (0.02 ml) is followed in 5 min by addition of aggregating agent (ADP or collagen suspension, 0.02 ml). Extent of aggregation, using ADP stimulus, or rate of aggregation, using collagen stimulus, is determined using the Payton Scientific Dual Channel Aggregation Module, Model 300B. Appropriate concentrations of ADP or collagen are determined by an initial brief titration.

Calculations

ADP-Induced Aggregation

The height in millimeters of aggregation curves for control aggregations (no drug addition, saline only) are compared with the heights of curves obtained after drug addition at various appropriate concentrations. Heights after drug addition are finally expressed as "percent of control" values. These values are plotted versus drug concentration on semilog paper. Estimates of $IC_{50}$ values are made from the resulting curves.

Collagen-Induced Aggregation

The major slope (that is, the slope of the first straight line portion) of the collagen-induced aggregation curve for each drug concentration is determined and compared to the slope of the curve for control aggregations. Values for drug test aggregations are expressed as "precent of control" and are plotted versus drug concentration on semilog paper. Estimates of $IC_{50}$ values are made from the resulting curves.

| Antithrombocyte Aggregation Evaluation for the Compound of Example 1 | | |
|---|---|---|
| | Platelet Rich Plasma | |
| $IC_{50}$ | ADP = | $6 \times 10^{-7}$ M |
| | Collagen = | $2 \times 10^{-7}$ M |
| | Whole Blood | |
| $IC_{50}$ | ADP = | $7 \times 10^{-10}$ M |
| | Collagen = | $5 \times 10^{-8}$ M |

Accordingly, the present invention also includes a pharmaceutical composition for treating psychoses, pain, sleep disorders, inflammation, or hypertension comprising a corresponding antipsychotic, analgesic, sleep inducing, anti-platelet aggregation, or antihypertensive effective amount of a compound of the Formula I as defined above together with a pharmaceutically acceptable carrier.

The present invention further includes a method for treating psychoses, pain, sleep disorders, blood clotting, or hypertension in mammals suffering therefrom comprising administering to such mammals either orally or parenterally a corresponding pharmaceutical composition containing a compound of the Formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium sterate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidfy.

Liquid form preparations include solutions, suspensions, and emulsions. As an example may be mentioned water or water propylene glycol solutions for paretneral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large armouns of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 0.01 mg to 500 mg preferably to 1 to 50 mg according to the particular application and the potency of the active ingredient. The compositions can, if desired, also contain other compatible therapeutic agents.

In therapeutic use as described above, the mammalian dosage range for a 70 kg subject is from 0.01 to 150 mg/kg of body weight per day or preferably 1 to 50 mg/kg of body weight per day. The dosages, however, may be varied depending upon the requirements of the patient, the severity of the condition being treated, and the compound being employed.

Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Examples further illustrate the invention.

PREPARATION I

5'-ETHYL CARBOXYLATE-INOSINE (A Compound of Formula IV wherein $R'_5$ is ethyl)

The acid (a compound of formula V wherein $R'_2$ and $R'_3$ are together propylidene) (32 g, 0.1 mol) is stirred in 100 ml thionyl chloride at 40° C. for 4 hours. The slurry is cooled to room temperature and diluted with 500 ml of diethyl ether. The solid is collected by filtration and dried overnight at room temperature. The solid is added, in one portion, to 1 L of vigorously stirred ethanol at 0° C. The solution is stirred for two hours while warming to room temperature then warmed to reflux for three hours. The ethanol is removed in vacuo and the residue dissolved in 300 ml of 50% formic acid and stirred at 50° C. for three hours. The formic acid is removed in vacuo and the residue recrystallized from 500 ml of ethanol to give 25.8 g (72%) of a white solid, the 5'-ethylcarboxylateinosine, mp=175°–177° C.d. Anal ($C_{12}H_{14}N_4O_6.0.5C_2H_5OH$); calc: C=46.85, H=5.14, N=16.81; found: C=42.86, H=4.63, N=16.79.

PREPARATION II

5'-ETHYL CARBOXYLATE-2',3'-DIACETYL-INOSINE

A Compound of Formula III, wherein $R'_5$ is ethyl, and $R'_2$ and $R'_3$ are Both Acetyl The 5'-ethyl carboxylate inosine as prepared in Preparation I above, (13.6, 44 mmol) is stirred in 50 ml pyridine and treated with acetic anhydride (10.1 g, 98 mmol). The solution is stirred for 24 hours at room temperature. The pyridine is removed in vacuo and the residue dissolved in 100 ml of methylene chloride. The solution is then washed successively with 1N HCl (100 ml), water (100 ml) and salt solution (100 ml). The solution is dried over magnesium sulfate and the solvent evaported in vacuo to give 13.3 (76%) of a white solid, the 5'-ethyl carboxylate-2',3'-diacetyl-inosine mp=205°–208° C. Anal. ($C_{16}H_{18}N_4O_8.0.6H_2O$); calc: C=47.43, H-4.78, N-13.82; found: C=47.31, H-4.35, N=13.83.

PREPARATION III

6-CHLORO-5'-ETHYL CARBOXYLATE-2',3' DIACETYL ADENOSINE (A compound of formula II wherein $R'_5$ is ethyl and $R'_2$ and $R'_3$ are both acetyl) The inosine analog as prepared in PREPARATION II above is placed in 300 ml acetonitile and tetraethyl ammonium chloride (10.8 g, 65 mmol) added. The solution is stirred and dimethyl aniline (3.9 g, 33 mmol) and phorphoroyl chloride (29.9 g, 194 mmol) are added. The new solution is placed in a 110° C. oil bath for 15 minutes. The solution is then immediately evaporated, so as to be free of volatile materials at 60° C. in vacuo. The remainder is dissolved in 300 ml of methylene chloride, poured over 500 ml ice/water and stirred for 30 minutes. This is repeated. Then the aqueous solution is extracated with methylene chloride (2×150 ml). The combined organic extraction mixtures are washed successively with 5% sodium bicarbonate (200 ml), water (200 ml) and saturated brine solution (200 ml). The mixtures are then dried over $MgSO_4$ and the solvent removed in vacuo to give a red oil. The oil is dissolved in ethylacetate and purified by chromatography to give, after evaporation of solvent from the appropriate fraction 9.7 (72%) of a clear oil, the 6-chloro-5'-ethyl carboxylate-2',3'-diacetyl adenosine, Anal ($C_{16}H_{17}ClN_4O_7$), calc: C=46.55, H=4.15, N=13.57, Cl=8.59; found: C=46.45, H=4.27, N=13.66, Cl=8.35.

EXAMPLE 1

(R)-N-6-[(2-phenyl-1-methyl) ethyl]-adenosine-5'-ethylcarboxamide (a compound of formula I wherein $R_6$ is (2-phenyl-1-methyl) ethyl, $R_8$ is $NR_3R_4$ wherein $R_3$ is hydrogen and $R_4$ is ethyl)

The 6-chloro adenosine analog as prepared in PREPARATION III above, (7.7 g, 18.6 mmol); triethylamine (1.9 g, 18.6 mmol) and 1-amphetamine (2.5 g, 18.6 mmol) are stirred in 125 ml of ethanol at reflux, overnight. The solution is cooled to 50° C. and sodium ethoxide (1.3 g, 18.6 mmol) added. The mixture is stirred at 50° C. for three hours. The solvents are then removed in vacuo and the residue stirred into 50 ml 5% $MeOH/CH_2Cl_3$ and purified by chromatography to give, after evaporation of solvent from the appropriate fraction, 1.9 g of a white foam. The foam is dissolved in 100 ml of ethanol and ethylamine (15 ml) added. The solution is stored at 0° C. overnight. The solution is evaporated free of solvent in vacuo and the residue dissolved in 15 ml of 5% MeOH/methylene chloride. The solution is purified by chromatography. Evaporation of the solvent from the appropriate fraction gave 1.4 g (20%) of a white foam, (R)-N-6-[(2-phenyl-1-methyl) ethyl]-adenosine-5'-ethyl-carboxamide, mp=151°–155° C.; Anal ($C_{21}H_{26}N_6O_4$); calc: C=59.14, H=6.15, N=19.71; found: C=59.31, H=6.23, N=19.63.

EXAMPLE 2

(R)-N-6-(1-indanyl) adenosine-5'-ethylcarboxamide (a compound of formula I wherein $R_6$ is indanyl and $R_8$ is $NR_3R_4$, wherein $R_3$ is hydrogen and $R_4$ is ethyl)

The title compound is synthesized in a manner similar to that of EXAMPLE 1 above from 6-chloro-5'-ethylcarboxylate-2',3'-diacetyl adenosine as prepared in PREPARATION III above, (4.6 g, 11.1 mmol), (R)-1-indanylamine (1.5 g, 11.1 mmol) and triethyl amine (1.3 g, 13 mmol). This gave, after amination of the intermediate ethyl ester with ethyl amine (15 ml), a wet foam that was dried by co-evaporation with 25 ml of acetone to give 0.45 g (10%) of a white solid, (R)-N-6-(1-indanyl) adenosine-5'-ethylcarboxamide, mp=135°–173° C.; Anal ($C_{21}H_{24}N_6O_4.0.25$ acetone); calc: C=59.51, H=5.86, N=19.14; found: C=59.76, H=5.86, N=19.08.

EXAMPLE 3

$N^6$-(2,2-diphenylethyl)-adenosine-5'-ethylcarboxamide (a compound of formula I wherein $R_6$ is 2,2-diphenylethyl and $R_8$ is $NR_3R_4$ wherein $R_3$ is hydrogen and $R_4$ is ethyl)

The title compound is synthesized in a manner similar to that of Example 1 using 6-chloro-5'-ethylcarboxylate-2',3'-diacetyl adenosine as prepared in PREPARATION III above, (2.2 g, 5.3 mmol), triethylamine (1.0 g, 10 mmol) and 2,2-diphenylethylamine (1.1 g, 5.5 mmol). This gave, after amination of the ethyl ester with ethyl amine (15 ml) and purification, 0.35 g (14%) of a white solid, N-6-(2,2-diphenylethyl)adenosine-5'-ethylcarboxamide mp=105°–110° C. Anal ($C_{26}H_{28}N_6O_4.0.3CH_2Cl_2$) calc: C=61.45, H=5.61, N=16.35; found: C=61.76, H=5.51, N=16.31.

EXAMPLE 4

N6-cyclopentyladenosine-5'-ethylcarboxamide (a compound of formula I wherein $R_6$ is cyclopentyl and $R_8$ is $NR_3R_4$ wherein $R_3$ is hydrogen and $R_4$ is ethyl).

The title compound was prepared in a manner similar to that for EXAMPLE 1 using 6-chloro-5'-ethylcarboxylate-2',3'-diacetyl adenosine as prepared in PREPARATION III above (7.7 g, 18.6 mmol) triethylamine (1.9 g, 18.6 mmol) and cyclopentylamine (1.8 g, 18.6 mmol). This gave, after amination of the ethyl ester with ethylamine (15 ml) and purification, 1.35 g (20%), of a white solid, N6-cyclopentyladenosine-5'-carboxamide, mp=95°–101° C. Anal ($C_{17}H_{24}N_6O_4$); calc: C=54.24, H=6.43, N=22.33; found: C=54.07; H=6.43, N=22.14.

EXAMPLE 5

N6-(2,2-diphenylethyl)-5-adenosine-5'-ethylcarboxylate (a compound of formula I wherein $R_6$ is 2,2-diphenylethyl and $R_8$ is $OR'_5$ wherein $R'_5$ is ethyl)

6-chloro-5'-ethylcarboxylate-2',3'-diacetyladenosine (2.2 g, 5.3 mmol), as prepared in PREPARATION III above, triethyl amine (1.0 g, 10 mmol) and 2,2-diphenyl ethylamine (1.1 g, 5.5 mmol) are stirred at reflux for four hours and then treated with an additional (1.1 g, 5.5 mmol) of 2,2-diphenylethylamine. The solution is stirred at reflux an additional hour then cooled to room temperature and stirred overnight. The solution is treated with sodium ethoxide (0.45 g, 6.5 mmol) and warmed to 50° C. for 1 hour. The solution is cooled to room temperature and the residue is dissolved in ethyl acetate (125 ml) and allowed to stand overnight. The solution is filtered free of insoluable material and purified by chromatography. The appropriate fractions are isolated by evaporation of solvent and dried on high vacuum overnight to give 0.5 g (19%) of pure ethyl ester (which was used to make the ethyl amide) and 0.9 g of impure mixture. The mixture was further purified by chromatography. The appropriate fraction was isolated by evaporation of solvent to give 0.55 g (21%) ((total yield 40%)) of a white solid, N6-(2,2-diphenylethyl)-5-adenosine-5'-ethylcarboxylate, mp=89°–95° C. Anal ($C_{26}H_{27}N_5O_5.0.4MeOH$); calc: C=63.12, H=5.74, N=13.94; found: C=62.87, H=5.62, N=14.00.

EXAMPLE 6

N-6-Naphthylmethyladenosine-5'-ethylcarboxamide (a compound of formula I where $R_6$ is naphthylmethyl and $R_8$ is $NR_3R_4$, wherein $R_3$ is hydrogen and $R_4$ is ethyl)

The title compound is synthesized in a manner similar to that of EXAMPLE 1 above from 6-chloro-5'-ethyl-carboxylate-2',3'-diacetyladenosine as prepared in PREPARATION III above, (4.8 g, 11.6 mmol), 1.82 g (11.6 mmol) 1-naphthylmethylamine, and 1.5 g triethylamine. This gave, after amination of the ethyl ester and purification, 1.1 g of the product as a white solid, mp 146-149 C. Analysis as $(C_{23}H_{24}N_6O_4 0.7CH_3OH)$ Calcd: C-60.45, H-5.73, N-17.85; Found: C-60.25, N-5.41, N-17.96.

EXAMPLE 7

(R)-N-6-[(2-Phenyl-1-methyl)ethyl]-adenosine-5'-ethyl-carboxylate (a compound of formula I wherein $R_6$ is (2-phenyl-1-methyl)ethyl, and $R_8$ is $OR_5'$ wherein $R_5'$ is ethyl)

The compound is prepared as in Example 1, stopping after the ethoxide deprotection and subsequent purification to give the title compound. Mp 63°-69° C. Analysis as $(C_{21}H_{25}N_5O_5)$ calcd: C-59.01, H-5.90, N-16.38; found: C-58.89, H-5.91, N-16.10.

EXAMPLE 8

N-6-Norbornyl-adenosine-5'ethylcarboxylate (a compound of formula I wherein $R_6$ is norbornyl and $R_8$ is $OR_5'$, wherein $R_5'$ is ethyl)

The title compound is synthesized in a manner similar to that of EXAMPLE 1 above from 6-chloro-5'-ethyl-carboxylate-2',3'-diacetyladenosine as prepared in PREPARATION III above, (7.5 g, 18.2 mmol), 2.2 g (20 mmol) endo-norbornylamine and 3.0 g triethylamine. After ethoxide deprotection and purification, the product was obtained as a white foam. Mp 75°-82° C. Analysis as $(C_{19}H_{25}N_5O_5 0.35CH_3OH)$ Calcd: C-56.05, H-6.42, N-16.89; found C-56.05, H-6.29, N-16.88.

EXAMPLE 9

N-6-Norbornyladenosine-5'ethylcarboxamide (a compound of formula I wherein $R_6$ is norbornyl and $R_8$ is $NR_3R_4$, wherein $R_3$ is H and $R_4$ is ethyl)

The title compound is synthesized in a manner similar to that of EXAMPLE 1 above from 6-chloro-5'-ethyl-carboxylate-2',3'-diacetyladenosine as prepared in PREPARATION III above, (7.5 g, 18.2 mmol), 2.2 g (20 mmol) endo-norbornylamine and 3.0 g triethylamine. After amination of the ethyl ester and purification, the product is obtained as a white foam. Mp 137°-141° C. Analysis as $(C_{19}H_{26}N_6O_4 0.25H_2O)$ calcd: C-56.07, H-6.56, N-20.65; found: C-56.15, H-6.57, N-20.56.

SCHEME I

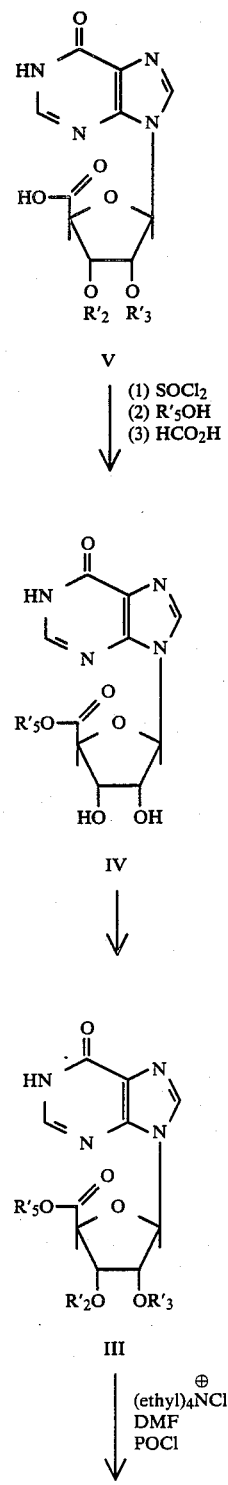

-continued
SCHEME I
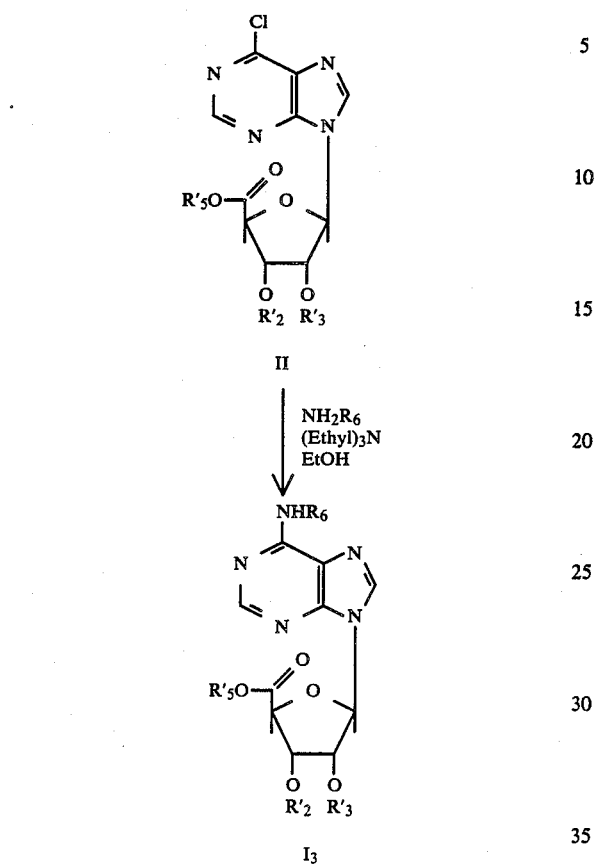
-continued
FORMULA
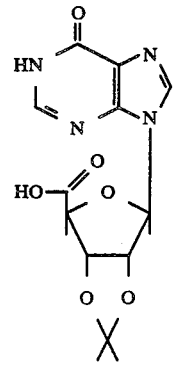
V
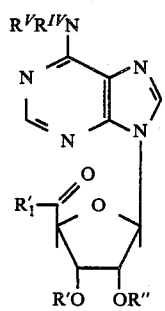
XXIII
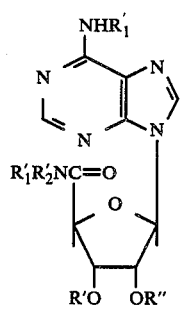
XXIV
FORMULA
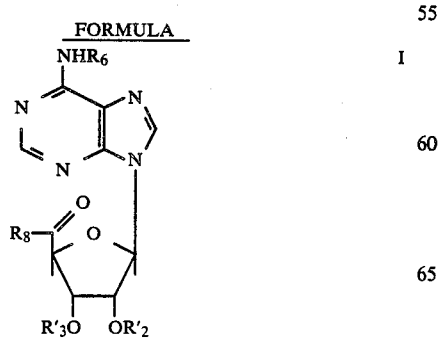
I
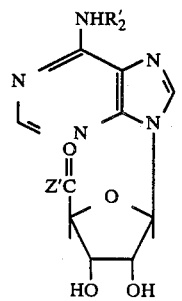
XXV
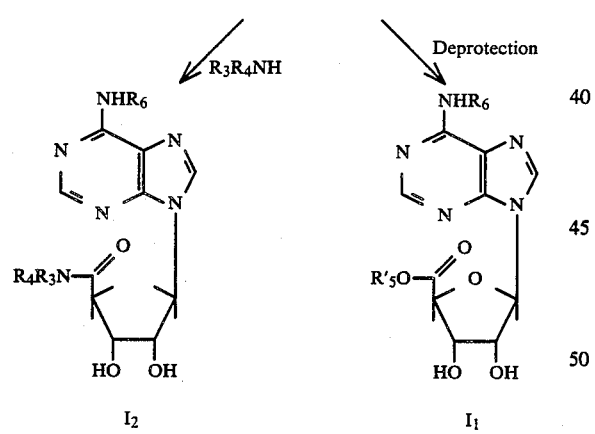

-continued
FORMULA

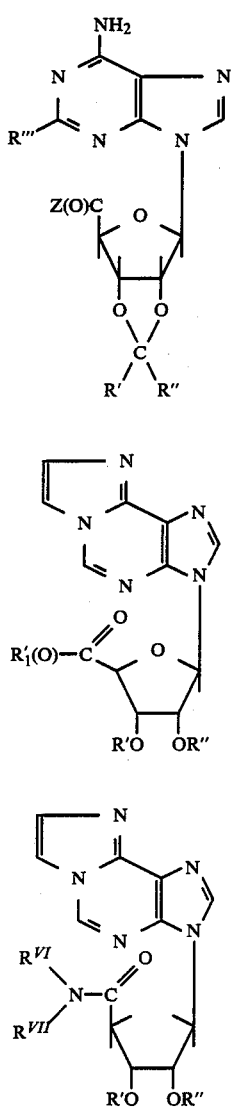

We claim:

1. A compound of the formula

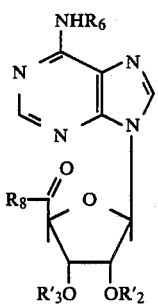

wherein (1) $R_6$ is (a)

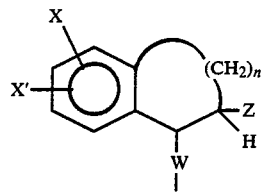

wherein in X and X' are each independently absent, lower alkyl, lower alkoxy, hydroxy, lower alkanoyl, carboalkoxy, nitro, halogen, amino, monoloweralkyl- or diloweralkyl-amino, or X and X' taken together are methylenedioxy; n is one to four; z is hydrogen, lower alkyl or OR wherein R is hydrogen, lower alkyl or lower alkanoyl; W is a bond or a straight or branched chain alkylene of from one to four carbon atoms with the proviso that W cannot be a bond when n is one;

(b)

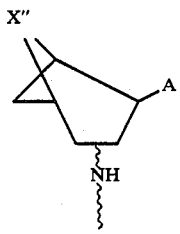

in which NH— is either endo or exo; A is hydrogen or methyl; X" is —C(CH₃)₂—, —CH₂—, —CH₂CH₂—, or —CH=CH;

(c)

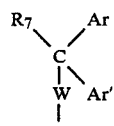

wherein $R_7$ is hydrogen, hydroxy, lower alkyl, lower carboalkoxy, or lower alkanoyloxy; W is as defined above and Ar and Ar' are each independently (i) phenyl, (ii) phenyl substituted by trifluoromethyl, halogen, hydroxy, thiol, lower alkoxy, lower alkanoyloxy, lower alkyl, nitro, amino, lower alkyl $S(O)_b$—wherein b is 0, 1 or 2, or sulfonamido, or (iii) 2-, 3-, or 4-pyridyl, 2- or 3-thienyl or 2- or 3-furanyl or (iv) naphthyl;

(2) $R'_2$ and $R'_3$ are each independently hydrogen, lower alkanoyl of from one to six carbons, benzoyl, benzoyl substituted by lower alkyl, lower alkoxy, halogen or $R'_2$ and $R'_3$ taken together complete a five-membered ring having a total of up to twenty carbons; and (3) $R_3$ is (a) $OR'_5$ wherein $R'_5$ is hydrogen, lower alkyl of from one to six carbons, or (b) $NR_3R_4$ wherein $R_3$ or $R_4$, are independently hydrogen, lower alkyl, or cycloalkyl of from three to seven ring carbons or a pharmaceutically acceptable acid addition salt thereof.

2. A compound of claim 1 wherein $R'_2$ and $R'_3$ are both H, alkanoyl benzoyl, or alkylidene.

3. A compound of claim 2 wherein $R_6$ is

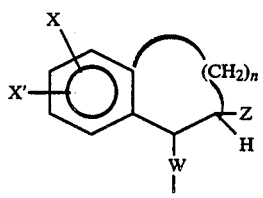

wherein X, X', Z, n, and W are as defined above.

4. A compound of claim 3 wherein X and X' are both absent, Z is hydrogen and n is 1.

5. A compound of claim 1 wherein $R_6$ is

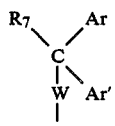

wherein $R_6$, Ar, Ar', and W are as defined above.

6. A compound of claim 5 wherein W is alkylene of from one to three carbons, Ar and Ar' are phenyl, and $R_7$ is hydrogen or lower alkyl.

7. A compound according to claim 6 and being N-6-(2,2-diphenylethyl)-adenosine-5'-ethylcarboxamide.

8. A compound according to claim 6 and being N-6-(2,2-diphenylethyl)-5-adenosine-5'-ethylcarboxylate.

9. A compound according to claim 1 wherein $R_6$ is

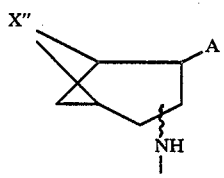

wherein A and X" are as defined above.

10. A pharmaceutical composition for treating hypertension comprising an antihypertensive effective amount of a compound as claimed in claim 1 together with a pharmaceutically acceptable carrier.

11. A method of treating hypertension in a mammal suffering therefrom, which comprises administering to such mammals an antihypertensive effective amount of a compound as claimed in claim 1 in unit dosage form.

12. A compound of the formula

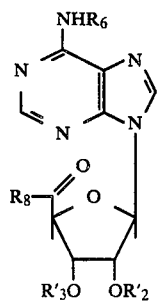

wherein $R_6$ is (a)

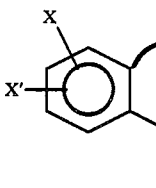

wherein X and X' are each independently absent, lower alkyl, lower alkoxy, hydroxy, lower alkanoyl, carboalkoxy, nitro, halogen, amino, monoloweralkyl- or diloweralkyl-amino, or X and X' taken together are methylenedioxy; n is one to four; z is hydrogen, lower alkyl or OR wherein R is hydrogen, lower alkyl or lower alkanoyl; W is a bond or a straight or branched chain alkylene of from one to four carbon atoms;

(b) cycloalkyl of from three to seven ring carbons or cycloalkyl of from three to seven ring carbons substituted by lower alkyl;

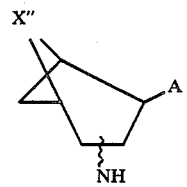

in which NH— is either endo or exo; X" is —C(CH$_3$)$_2$—, —CH$_2$—, —CH$_2$CH$_2$—, or —CH=CH;

(d)

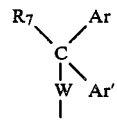

wherein $R_7$ is hydrogen, hydroxy, lower alkyl, lower carboalkoxy, or lower alkanoyloxy; W is as defined above and Ar and Ar' are each independently (i) phenyl, (ii) phenyl substituted by trifluoromethyl, halogen, hydroxy, thiol, lower alkoxy, lower alkanoyloxy, lower alkyl, nitro, amino, lower alkyl-S(O)$_b$ wherein b is 0, 1, or 2, sulfonamido, or (iii) 2-, 3-, or 4-pyridyl, 2- or 3-thienyl or 2- or 3-furanyl or (IV) naphthyl; or (e)

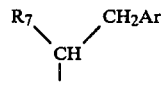

wherein $R_7$ and Ar are as defined above;

(2) $R'_2$ and $R'_3$ are each independently hydrogen, lower alkanoyl, benzoyl, benzoyl substituted by lower alkyl, lower alkoxy, halogen or $R'_2$ and $R'_3$ taken together are a five-membered ring having a total of up to twenty carbons; and (3) $R_8$ is (a) $OR'_5$ wherein $R'_5$ is cycloalkyl of from three to seven carbons optionally substituted by lower alkyl; a diastereomer, or a pharmaceutically acceptable acid addition salt thereof.

13. A compound of claim 12 wherein $R_6$ is cycloalkyl of from 3 to 7 carbons optionally substituted by lower alkyl.

14. A pharmaceutical composition for a favorable ratio of affinities for adenosine receptors designated AI and AII comprising a therapeutically effective amount of a compound as claimed in claim 12 together with a pharmaceutically acceptable carrier.

15. A method of treating hypertension in a mammal suffering therefrom which comprises administering to such mammal a compound as claimed in claim 12 in unit dosage form.

* * * * *